(12) United States Patent
Mault

(10) Patent No.: US 7,392,193 B2
(45) Date of Patent: Jun. 24, 2008

(54) SPEECH RECOGNITION CAPABILITY FOR A PERSONAL DIGITAL ASSISTANT

(75) Inventor: James R Mault, Evergreen, CO (US)

(73) Assignee: Microlife Corporation, Taipei (TW)

( * ) Notice: Subject to any disclaimer, the term of this patent is extended or adjusted under 35 U.S.C. 154(b) by 756 days.

(21) Appl. No.: 10/311,414

(22) PCT Filed: Jun. 18, 2001

(86) PCT No.: PCT/US01/41031

§ 371 (c)(1),
(2), (4) Date: Dec. 31, 2002

(87) PCT Pub. No.: WO01/97211

PCT Pub. Date: Dec. 20, 2001

(65) Prior Publication Data

US 2003/0163321 A1 Aug. 28, 2003

Related U.S. Application Data

(60) Provisional application No. 60/212,319, filed on Jun. 16, 2000.

(51) Int. Cl.
*G10L 21/00* (2006.01)
(52) U.S. Cl. .................. 704/275; 704/270; 704/231; 600/300; 705/26
(58) Field of Classification Search ............... 704/231, 704/270, 275; 600/300; 705/26
See application file for complete search history.

(56) References Cited

U.S. PATENT DOCUMENTS

| | | | |
|---|---|---|---|
| 2,630,798 A | 3/1953 | White et al. ............... 128/2.07 |
| 2,826,912 A | 3/1958 | Kritz ........................... 73/194 |
| 2,831,348 A | 4/1958 | Kritz ........................ 73/861.28 |
| 2,838,399 A | 6/1958 | Vogel, Jr. ...................... 99/48 |
| 2,869,357 A | 11/1959 | Kritz ............................. 73/32 |
| 2,911,825 A | 11/1959 | Kritz ........................... 73/194 |

(Continued)

FOREIGN PATENT DOCUMENTS

DE     198 10 476 A1    9/1998

(Continued)

OTHER PUBLICATIONS

Medical Progress Through Technology, vol. 9, No. 1, 1982 Berlin (D), pp. 27-32, R. Salminen et al., "Computerized Breath-by-Breath Analysis of Respiratory Variables During Exercise".

(Continued)

*Primary Examiner*—Vijay B Chawan
(74) *Attorney, Agent, or Firm*—Courtney Staniford & Gregory LLP

(57) ABSTRACT

A speech recognition module for a personal digital assistant comprises: a module housing designed to engage with an accessory feature of the PDA, such as an accessory slot; a microphone for receiving speech commands from the person; and a speech recognition system. A corresponding electrical speech command signal is communicated to the portable computing device, allowing control of the operation of a software application program running on the portable computing device. In particular, menu items can be selected for generation of a diet log for the person, for example during a weight control program.

18 Claims, 5 Drawing Sheets

U.S. PATENT DOCUMENTS

| | | | |
|---|---|---|---|
| 2,920,012 A | 1/1960 | Sanders et al. | 167/51.5 |
| 3,213,684 A | 10/1965 | Seaton et al. | 73/190 |
| 3,220,255 A | 11/1965 | Scranton et al. | 73/204 |
| 3,250,270 A | 5/1966 | Bloom | 128/2.07 |
| 3,306,283 A | 2/1967 | Arp | 128/2.07 |
| 3,523,529 A | 8/1970 | Kissen | 128/2.07 |
| 3,527,205 A | 9/1970 | Jones | 128/2.08 |
| 3,681,197 A | 8/1972 | Smith | 195/63 |
| 3,726,270 A | 4/1973 | Griffis et al. | 128/2.08 |
| 3,799,149 A | 3/1974 | Rummel et al. | 128/2.07 |
| 3,814,091 A | 6/1974 | Henkin | 128/188 |
| 3,834,375 A | 9/1974 | Sanctuary et al. | 128/2.07 |
| 3,895,630 A | 7/1975 | Bachman | 128/2.07 |
| 3,938,551 A | 2/1976 | Henkin | 137/613 |
| 3,962,917 A | 6/1976 | Terada | 73/204 |
| 3,972,038 A | 7/1976 | Fletcher et al. | 340/189 M |
| 3,979,480 A | 9/1976 | Radici et al. | 525/425 |
| 3,991,304 A | 11/1976 | Hillsman | 235/151.34 |
| 4,003,396 A | 1/1977 | Fleischmann | 137/83 |
| 4,051,847 A | 10/1977 | Henkin | 128/145.6 |
| 4,078,554 A | 3/1978 | Lemaitre et al. | 128/2.08 |
| 4,095,274 A | 6/1978 | Gordon | 364/715 |
| 4,100,401 A | 7/1978 | Tutt et al. | 235/92 T |
| 4,101,071 A | 7/1978 | Brejnik et al. | 235/92 MT |
| 4,117,834 A | 10/1978 | McPartland et al. | 128/2 S |
| 4,151,668 A | 5/1979 | Hungerford | 40/495 |
| 4,159,416 A | 6/1979 | Brejnik et al. | 235/92 MT |
| 4,186,735 A | 2/1980 | Henneman et al. | 128/201.25 |
| 4,188,946 A | 2/1980 | Watson et al. | 128/204.22 |
| 4,192,000 A | 3/1980 | Lipsey | 364/415 |
| 4,197,857 A | 4/1980 | Osborn | 600/531 |
| 4,200,094 A | 4/1980 | Gedeon et al. | 128/201.13 |
| 4,211,239 A | 7/1980 | Raemer et al. | 128/716 |
| 4,212,079 A | 7/1980 | Segar et al. | 364/900 |
| 4,221,224 A | 9/1980 | Clark | 128/718 |
| 4,221,959 A | 9/1980 | Sessler | 377/13 |
| 4,224,952 A | 9/1980 | Sidorenko et al. | 128/782 |
| 4,230,108 A | 10/1980 | Young | |
| 4,244,020 A | 1/1981 | Ratcliff | 364/413 |
| 4,321,674 A | 3/1982 | Krames et al. | 364/413 |
| 4,341,867 A | 7/1982 | Johansen | 435/189 |
| 4,353,375 A | 10/1982 | Colburn et al. | 128/782 |
| 4,359,057 A | 11/1982 | Manzella | 128/718 |
| 4,368,740 A | 1/1983 | Binder | 128/718 |
| 4,380,802 A | 4/1983 | Segar et al. | 364/900 |
| 4,386,604 A | 6/1983 | Hershey | 128/718 |
| 4,387,777 A | 6/1983 | Ash | 177/43 |
| 4,425,805 A | 1/1984 | Ogura et al. | 73/861.29 |
| 4,440,177 A | 4/1984 | Anderson et al. | 600/532 |
| 4,444,201 A | 4/1984 | Itoh | 128/716 |
| 4,463,764 A | 8/1984 | Anderson et al. | 600/532 |
| 4,545,023 A | 10/1985 | Mizzi | 364/709 |
| 4,566,461 A | 1/1986 | Lubell et al. | 128/668 |
| 4,571,682 A | 2/1986 | Silverman et al. | 364/413 |
| 4,572,208 A | 2/1986 | Cutler et al. | 128/718 |
| 4,575,804 A | 3/1986 | Ratcliff | 364/715 |
| 4,598,700 A | 7/1986 | Tamm | 128/671 |
| 4,608,995 A | 9/1986 | Linnarsson et al. | 128/713 |
| 4,619,269 A | 10/1986 | Cutler et al. | 128/719 |
| 4,629,015 A | 12/1986 | Fried et al. | 177/25 |
| 4,648,396 A | 3/1987 | Raemer | 600/534 |
| 4,650,218 A | 3/1987 | Hawke | 283/67 |
| 4,658,832 A | 4/1987 | Brugnoli | 600/532 |
| 4,686,624 A | 8/1987 | Blum et al. | 364/415 |
| 4,709,331 A | 11/1987 | Barkett et al. | 364/413 |
| 4,731,726 A | 3/1988 | Allen, III | 364/416 |
| 4,753,245 A | 6/1988 | Gedeon | 128/718 |
| 4,756,670 A | 7/1988 | Arai | 417/43 |
| 4,757,453 A | 7/1988 | Nasiff | 364/415 |
| 4,781,184 A | 11/1988 | Fife | 128/205.12 |
| 4,796,182 A | 1/1989 | Duboff | 364/413.29 |
| 4,796,639 A | 1/1989 | Snow et al. | 600/532 |
| 4,803,625 A | 2/1989 | Fu et al. | 364/413.03 |
| 4,807,169 A | 2/1989 | Overbeck | 364/715.01 |
| 4,823,808 A | 4/1989 | Clegg et al. | 128/773 |
| 4,850,371 A | 7/1989 | Broadhurst et al. | 600/532 |
| 4,853,854 A | 8/1989 | Behar et al. | 364/413.01 |
| 4,855,942 A | 8/1989 | Bianco | 364/561 |
| 4,855,945 A | 8/1989 | Sakai | 364/709.02 |
| 4,856,531 A | 8/1989 | Merilainen | 600/532 |
| 4,891,756 A | 1/1990 | Williams, III | 364/413.29 |
| 4,894,793 A | 1/1990 | Ikemoto et al. | 364/709.03 |
| 4,909,259 A | 3/1990 | Tehrani | 600/531 |
| 4,911,256 A | 3/1990 | Attikiouzel | 177/25.16 |
| 4,914,959 A | 4/1990 | Mylvaganam et al. | 73/861.28 |
| 4,917,108 A | 4/1990 | Mault | 128/718 |
| 4,924,389 A | 5/1990 | Gerbaulet et al. | 364/413.29 |
| 4,951,197 A | 8/1990 | Mellinger | 364/413.2 |
| 4,954,954 A | 9/1990 | Madsen et al. | 364/413.29 |
| 4,955,946 A | 9/1990 | Mount et al. | 600/532 |
| 4,966,155 A | 10/1990 | Jackson | 128/671 |
| 4,986,268 A | 1/1991 | Tehrani | 128/204 |
| 4,998,018 A | 3/1991 | Kurahashi et al. | 250/343 |
| 5,012,411 A | 4/1991 | Policastro et al. | 364/413.06 |
| 5,020,107 A * | 5/1991 | Rohani et al. | 704/275 |
| 5,022,406 A | 6/1991 | Tomlinson | 128/719 |
| 5,033,561 A | 7/1991 | Hettinger | 177/25.16 |
| 5,038,773 A | 8/1991 | Norlien et al. | 128/205.23 |
| 5,038,792 A | 8/1991 | Mault | 128/718 |
| 5,042,500 A | 8/1991 | Norlien et al. | 600/532 |
| 5,042,501 A | 8/1991 | Kenny et al. | 600/532 |
| 5,060,506 A | 10/1991 | Douglas | 73/24.1 |
| 5,060,655 A | 10/1991 | Rudolph | 128/716 |
| 5,060,656 A | 10/1991 | Howard | 128/718 |
| 5,069,220 A | 12/1991 | Casparie et al. | 128/719 |
| 5,072,737 A | 12/1991 | Goulding | 128/718 |
| 5,081,871 A | 1/1992 | Glaser | 73/863.23 |
| 5,095,900 A | 3/1992 | Fertig et al. | 128/207.14 |
| 5,095,913 A | 3/1992 | Yelderman et al. | 128/719 |
| 5,117,674 A | 6/1992 | Howard | 73/31.07 |
| 5,119,825 A | 6/1992 | Huhn | 600/529 |
| 5,173,588 A | 12/1992 | Harrah | 235/114 |
| 5,178,155 A | 1/1993 | Mault | 128/718 |
| 5,179,958 A | 1/1993 | Mault | 128/718 |
| 5,214,966 A | 6/1993 | Delsing | 73/861.28 |
| 5,233,520 A | 8/1993 | Kretsch et al. | 364/413.29 |
| 5,233,996 A | 8/1993 | Coleman et al. | 600/529 |
| 5,263,491 A | 11/1993 | Thornton | 128/774 |
| 5,282,473 A | 2/1994 | Braig et al. | 600/532 |
| 5,285,794 A | 2/1994 | Lynch | 128/719 |
| 5,293,875 A | 3/1994 | Stone | 128/719 |
| 5,299,579 A | 4/1994 | Gedeon et al. | 600/532 |
| 5,303,712 A | 4/1994 | Van Duren | 600/529 |
| 5,307,263 A | 4/1994 | Brown | 364/413.09 |
| 5,309,921 A | 5/1994 | Kisner et al. | 600/532 |
| 5,326,973 A | 7/1994 | Eckerbom et al. | 250/343 |
| 5,355,879 A | 10/1994 | Brain | |
| 5,363,857 A | 11/1994 | Howard | 600/531 |
| 5,367,972 A | 10/1994 | Norlien | 128/725 |
| 5,387,164 A | 2/1995 | Brown, Jr. | 482/9 |
| 5,388,043 A | 2/1995 | Hettinger | 364/413.29 |
| 5,398,688 A | 3/1995 | Laniado | 128/660.02 |
| 5,398,695 A | 3/1995 | Anderson et al. | 600/532 |
| 5,402,796 A | 4/1995 | Packer et al. | 128/719 |
| 5,412,560 A | 5/1995 | Dennisson | 364/413.01 |
| 5,412,564 A | 5/1995 | Ecer | 364/413.29 |
| 5,419,326 A | 5/1995 | Harnoncourt | 128/660.02 |
| 5,425,374 A | 6/1995 | Ueda et al. | 600/532 |
| 5,450,193 A | 9/1995 | Carlsen et al. | 356/301 |
| 5,454,721 A | 10/1995 | Kuch | 434/127 |
| 5,468,961 A | 11/1995 | Gradon et al. | 250/345 |
| 5,478,989 A | 12/1995 | Shepley | 235/375 |
| 5,485,402 A | 1/1996 | Smith et al. | 364/566 |
| 5,503,151 A | 4/1996 | Harnoncourt et al. | 128/660.02 |

| | | | | |
|---|---|---|---|---|
| 5,524,169 A * | 6/1996 | Cohen et al. ............... 704/231 |
| 5,542,420 A | 8/1996 | Goldman et al. ............ 128/630 |
| 5,570,697 A | 11/1996 | Walker et al. ............... 128/719 |
| 5,632,281 A | 5/1997 | Rayburn ...................... 128/719 |
| 5,640,774 A | 6/1997 | Goldman .................... 33/15 D |
| 5,645,071 A | 7/1997 | Harnoncourt et al. ....... 128/719 |
| 5,647,370 A | 7/1997 | Harnoncourt ............... 128/725 |
| 5,673,691 A * | 10/1997 | Abrams et al. .............. 600/300 |
| 5,676,132 A | 10/1997 | Tillotson et al. ....... 128/204.23 |
| 5,678,562 A | 10/1997 | Sellers ........................ 128/710 |
| 5,691,927 A | 11/1997 | Gump .................... 364/709.01 |
| 5,704,350 A | 1/1998 | Williams, III ............... 128/630 |
| 5,705,735 A | 1/1998 | Acorn .......................... 73/23.3 |
| 5,722,418 A | 3/1998 | Bro ............................. 128/732 |
| 5,729,479 A | 3/1998 | Golan .................... 364/709.02 |
| 5,749,072 A | 5/1998 | Mazurkiewicz et al. ..... 704/275 |
| 5,754,288 A | 5/1998 | Yamamoto et al. .......... 356/301 |
| 5,788,655 A | 8/1998 | Yoshimura et al. .......... 600/587 |
| 5,789,660 A | 8/1998 | Kofoed et al. ................ 73/232 |
| 5,796,009 A | 8/1998 | Delsing ................... 73/861.28 |
| 5,800,360 A | 9/1998 | Kisner et al. ................ 600/532 |
| 5,810,722 A | 9/1998 | Heikkila ..................... 600/300 |
| 5,816,246 A | 10/1998 | Mirza .......................... 128/726 |
| 5,819,735 A | 10/1998 | Mansfield et al. ........... 128/630 |
| 5,822,715 A | 10/1998 | Worthington et al. ......... 702/19 |
| 5,827,179 A | 10/1998 | Lichter et al. ............... 600/300 |
| 5,828,943 A | 10/1998 | Brown ........................ 434/258 |
| 5,831,175 A | 11/1998 | Fletcher-Haynes ....... 73/851.28 |
| 5,832,448 A | 11/1998 | Brown ............................ 705/2 |
| 5,834,626 A | 11/1998 | DeCastro et al. ............. 73/23.3 |
| 5,836,300 A | 11/1998 | Mault .................... 128/204.23 |
| 5,836,312 A | 11/1998 | Moore ........................ 128/897 |
| 5,839,901 A | 11/1998 | Karkanen ................... 434/127 |
| 5,841,115 A | 11/1998 | Shepley ...................... 235/375 |
| 5,845,263 A | 12/1998 | Camaisa et al. ............... 705/27 |
| 5,876,351 A | 3/1999 | Rohde ........................ 600/523 |
| 5,890,128 A | 3/1999 | Diaz et al. ...................... 705/2 |
| 5,899,855 A | 5/1999 | Brown ........................ 600/301 |
| 5,908,301 A | 6/1999 | Lutz ............................ 434/236 |
| 5,913,310 A | 6/1999 | Brown ........................ 128/897 |
| 5,918,603 A | 7/1999 | Brown ........................ 128/897 |
| 5,922,610 A | 7/1999 | Alving et al. ............... 436/116 |
| 5,932,812 A | 8/1999 | Delsing ................... 73/861.02 |
| 5,933,136 A | 8/1999 | Brown ........................ 345/327 |
| 5,951,300 A | 9/1999 | Brown ........................ 434/236 |
| 5,954,510 A | 9/1999 | Merrill et al. ............... 434/236 |
| 5,954,640 A | 9/1999 | Szabo ......................... 600/300 |
| 5,957,858 A | 9/1999 | Micheels et al. ............ 600/532 |
| 5,987,493 A | 11/1999 | Rangan et al. .............. 709/105 |
| 5,989,188 A | 11/1999 | Birkhoelzer et al. ........ 600/300 |
| 5,989,200 A | 11/1999 | Yoshimura et al. .......... 600/587 |
| 5,997,476 A | 12/1999 | Brown ........................ 600/300 |
| 6,010,459 A | 1/2000 | Silkoff et al. ................ 600/532 |
| 6,013,007 A | 1/2000 | Root ............................... 482/8 |
| 6,014,578 A | 1/2000 | Minoz ........................ 600/350 |
| 6,024,281 A | 2/2000 | Shepley ...................... 235/375 |
| 6,024,699 A | 2/2000 | Surwit et al. ................ 600/300 |
| 6,030,342 A | 2/2000 | Amano et al. ............... 600/301 |
| 6,032,119 A | 2/2000 | Brown et al. ................... 705/2 |
| 6,032,676 A | 3/2000 | Moore ........................ 128/898 |
| 6,039,688 A | 3/2000 | Douglas et al. ............. 600/300 |
| 6,040,531 A | 3/2000 | Miller-Kovach et al. . 177/25.16 |
| 6,042,383 A | 3/2000 | Herron ........................ 434/238 |
| 6,044,843 A | 4/2000 | O'Neil et al. .......... 128/204.23 |
| 6,045,513 A | 4/2000 | Stone et al. ................. 600/508 |
| 6,077,193 A | 6/2000 | Buhler et al. .................. 482/8 |
| 6,083,006 A | 7/2000 | Coffman ..................... 434/127 |
| 6,095,949 A | 8/2000 | Arai ............................... 482/4 |
| 6,095,985 A | 8/2000 | Raymond et al. ........... 600/513 |
| 6,101,478 A | 8/2000 | Brown ............................ 705/2 |
| 6,135,107 A | 10/2000 | Mault .................... 128/204.23 |
| 6,135,950 A | 10/2000 | Adams ........................ 600/300 |
| 6,135,951 A | 10/2000 | Richardson et al. ......... 600/300 |
| 6,139,494 A | 10/2000 | Cairnes ...................... 600/300 |
| 6,149,062 A * | 11/2000 | Danielson et al. ....... 235/472.01 |
| 6,167,255 A | 12/2000 | Kennedy, III et al. ....... 455/414 |
| 6,219,560 B1 | 4/2001 | Erkkila et al. ............... 455/557 |
| 6,277,645 B1 | 8/2001 | Mault ......................... 436/133 |
| 6,309,360 B1 | 10/2001 | Mault ......................... 600/531 |
| 6,402,698 B1 | 6/2002 | Mault ......................... 600/532 |
| 6,453,371 B1 * | 9/2002 | Hampson et al. .............. 710/37 |
| 6,468,222 B1 | 10/2002 | Mault et al. ................. 600/531 |
| 6,478,736 B1 | 11/2002 | Mault ......................... 600/300 |
| 6,513,532 B2 | 2/2003 | Mault et al. ................. 128/921 |

FOREIGN PATENT DOCUMENTS

| | | |
|---|---|---|
| EP | 0 459 647 A2 | 12/1991 |
| EP | 0 712 638 A1 | 7/1995 |
| GB | 2 323 292 A | 9/1998 |
| WO | 96/40340 | 12/1996 |

OTHER PUBLICATIONS

British Journal of Anaesthesia, vol. 49, 1977 London (GB) pp. 575-587, J.A. Bushman et al. "Closed Circuit Anaesthesia."

IEEE Transactions on Biomedical Engineering, vol. 35, No. 9, Sep. 1988, pp. 653-659, Capek et al. "Noninvasive Measurement of Cardiac Output Using Partial CO2 ReBreathing".

Clinics in Chest Medicine (Review) vol. 10, 1989, pp. 255-264, Heigenhauser et al., "Measurement of Cardiac Output by Carbon Dioxide Rebreathing Methods".

Biochemical, Pharmacological, and Clinical Aspects of Nitric Oxide, G. Gabor and N. Allon, Plenum Press, New York, 1995 "Determination of Nitric Oxide Levels by Fluorescence Spectroscopy."

* cited by examiner

SPEECH RECOGNITION CAPABILITY FOR A PERSONAL DIGITAL ASSISTANT

FIELD OF THE INVENTION

The invention relates to speech recognition capabilities of a computing device. In particular, the invention relates to the use of speech recognition in creating a diet log for a person on a weight control program.

BACKGROUND OF THE INVENTION

Portable computing devices such as personal digital assistants (PDAs), including Palm Pilots, Handspring Visors, hand-held PCs, and similar devices, have become incredibly popular because of their functionality and flexibility. For purposes of this application, the term computing device should be understood to include all computing devices, including those with additional functionality, including: desk-top, laptop, hand-held, palm top and wearable computers; and also cellular phones, telephones, two-way paging devices, radios, communicators, calculators, organizers, e-books, navigation devices, automobile electronics, digital interactive television controllers, and other electronic devices having computing capability. However, for ease of description, this application will focus on portable computing devices such as the Palm Pilot family of hand-held devices (Palm Inc., Santa Clara, Calif.) and the Handspring Visor (Handspring, Mountain View, Calif.).

These personal digital assistants (or PDAs) include buttons and touch sensitive screens allowing input of data in a variety of ways, including various forms of handwriting recognition and simplified keyboards. For some persons and applications, these forms of data input are insufficient. For example, a person who wishes to input information, such as recording what meals were eaten during a day or expenses incurred on a trip, must grasp an input stylus with one hand while holding the PDA in the other hand. The stylus is then used to touch the touch sensitive screen in a manner indicative of the input desired. This obviously ties up both of the person's hands, and requires a moderate level of visual and mental focus. It would be more desirable if data input could be made using a person's voice, rather than manual manipulation.

A partial solution is offered by some hand-helds which include voice recording capability. A person who wishes to quickly record information on the PDA presses a record button and speaks into a microphone. Later, the recorded information may be played back. Unfortunately, this approach falls far short of what is desirable. The voice recording is only voice-to-voice and therefore someone must later listen to the recorded voice and manually input the data. While the original recording step may be easier than manual manipulation, manual manipulation is not avoided because it must be completed at a later time. More desirable would be a voice-to-text voice recognition capability so that a person may speak commands and information and the PDA responds to the commands and records the information in text form. However, voice-to-text speech recognition is extremely complex and requires powerful computer processors and a large data storage capability. Current PDAs offer only a fraction of the necessary processing power and storage.

Speech recognition software and systems are well known in the art, for example as described in U.S. Pat. Nos. 5,749,072 to Mazurkiewicz et al., and 6,167,255 to Kennedy III et al, incorporated herein by reference.

SUMMARY OF THE INVENTION

According to the present invention, the limitations of currently available computing devices (such as portable computing devices including PDAs) and speech recognition software are overcome by offering a simplified speech recognition program and software designed to work with this simplified speech recognition capability. Much of the complexity of speech recognition software comes from the huge variety of words in a given language and the similarity in sounds of many of these words. The software must be capable of very accurately capturing the spoken sounds. Then, the software must determine what word was spoken out of a variety of similar choices by analyzing the context of the word, statistical likelihood, and past usage by a given person. Also, persons do not consistently pronounce words so software must be "trained" to recognize a specific person. The speech recognition challenge is significantly reduced by artificially constraining the vocabulary the software and hardware must interpret. Examples of restricted vocabulary speech recognition are currently used on many telephone systems, allowing persons to either press a number 0 through 9 or to speak the number. In this situation, the speech recognition software must only recognize and distinguish between ten choices, all of which are reasonably distinct.

According to the present invention, a similar capability is provided to PDAs. In a preferred embodiment, the PDA is capable of recognizing numbers 0 through 9 when they are spoken by a person. Current PDAs do not have this hardware or software capability. However, software may be added to most PDAs. Also, most PDAs are capable of accepting add-on hardware modules. For example, the Handspring Visor has a slot arrangement on its back side known as a Springboard. A variety of hardware modules, such as memory modules, may be inserted into the Springboard to enhance the capability of the Handspring Visor. Likewise, the Palm Pilot family of hand-held PDAs accept clip-on hardware modules to enhance their capabilities. It is expected that future versions of PDAs will include new and simplified hardware attachment capabilities.

Typically, a hardware module which is inserted into or attached to a PDA may also include application software further enhancing the capabilities of the PDA and taking advantage of the additional hardware. For example, the Handspring Visor accepts numerous Springboard compatible hardware modules, such as digital camera modules and music recording and playback modules. These modules interconnect with the Springboard portion of the Handspring Visor and include hardware such as a digital camera lens and related electronics, or music recording and playback hardware. This add-on hardware cooperates with the existing capabilities of the Handspring Visor to provide the capabilities of a digital camera or digital music player and recorder. The hardware modules also include onboard software which is accessed and used by the hardware of the Handspring Visor and the add-on hardware module. The software allows the module and Handspring Visor to communicate and provide the enhanced capabilities. Likewise, hardware modules such as wireless modems may be interconnected with some members of the Palm Pilot family.

A speech recognition module for a personal digital assistant comprises: a module housing configured to engage with an accessory feature of the PDA; a speech receiving device for receiving speech commands from the person; and a speech recognition means capable of distinguishing multiple speech commands and communicating a corresponding set of electrical commands to the PDA. Further, the speech recognition module for a portable computing device can comprise: a module housing configured to engage with an accessory interface of the portable computing device; a speech receiving device, adapted to receive a speech command from the person and to provide an electrical speech signal; and a speech recognition system, adapted to receive the electrical speech signal from the speech receiving device, to distinguish the speech command, and to communicate a corresponding electrical speech command signal to the portable computing device, wherein the electrical speech command signal is used to control the operation of a software application program running on the portable computing device. The speech receiving device can be a microphone. Speech recognition of microphone signals is disclosed in U.S. Pat. No. 5,749,072 to Mazurkiewicz et al., for example with reference to FIG. 3 of that patent. The module can further comprise a nutritional database of food item identifiers and associated nutritional data for a number of food items. Nutritional data can comprise calorie content, fat content, fiber content, protein content, glycemic index, mineral content, vitamin content, and other nutritional components associated with each of the food item identifiers. The software application program can be adapted to select a selected food item identifier from the nutritional database under control of the electrical speech command signal, and to store the selected food item identifier and associated nutritional data in a memory so as to create a diet log for the person.

A portable computing system according to the present invention comprises: a display; a microprocessor; a memory; a database of nutritional data relating to each of a plurality of food item identifiers; a speech recognition system providing an electrical speech command signal correlated with a spoken input; and a software application program, executed by the microprocessor, adapted to display a food menu of food item identifiers on the display, to select a food item identifier from the food menu based on the electrical speech command signal received from the speech recognition system, and to store nutritional data relating to the selected food item identifier in the memory so as to create a diet log of selected food items. The nutritional database can be arranged in a hierarchical form in that particular food items are characterized by a generic type, and in the software application program can be further adapted to display a menu of generic types on the display, and to select a generic type from the menu of generic types on receipt of the electrical speech signal.

An improved accessory module for a portable computing device (the combined system which can then be used for diet logging as part of a weight control program) comprises: an electrical interface, adapted to communicate with an accessory port of the portable computing device; a memory; a nutritional database, stored in the memory, correlating each of a number of food item identifiers with an associated food item nutritional content; and a software application program, stored in the memory, and executable by the microprocessor so as to present a menu of food item identifiers on the display, further adapted to select a food item selection from the menu of food item identifiers on receipt of a speech command signal, and further adapted to store the food item selection and correlated nutritional content within a diet log for the person. Nutritional content may included calorie content, diet component content, and other nutritional component of the food item. The speech command signal can be provided by a speech recognition system resident on the accessory module, on the portable computing device, or on another device in communication with the portable computing device.

A method of creating a diet log for a person, comprises: presenting a menu of food type identifiers to the person; receiving a type selection speech command from the person; correlating the type selection speech command with a selected food type identifier; presenting a menu of food item identifiers to the person, wherein the food item identifiers have a hierarchical relationship to the selected food type identifier; receiving an item selection speech command from the person; correlating the item selection speech command with a selected food item identifier; and storing the selected food item identifier and associated nutritional data within a memory device, so as to create a diet log for the person. The selected food item identifier is correlated with associated nutritional data using a nutritional database. The menus can be presented to the person on the display of a portable electronic device carried by the person, such as a personal digital assistant (PDA), other portable computing device, wrist-mounted device, wearable computer system, electronic book, electronic notebook, digital organizer, wireless phone, desktop computer system, web-TV, digital interactive TV, tablet computer, visor-mounted display system, or the like. The menus presented to the person can be chosen based on the physical location of the person, for example as input by the person, as transmitted from a local wireless network, or as determined by a position location system such as a global positioning system (GPS). The correlation of speech commands with selected identifiers can performed by a software application program ruining on the portable computing device, accessory module to the portable computing device, or other device in communication with the portable computing device such as a remote computer system in communication with the portable computing device over a communications network.

In other embodiments, spoken commands can be recorded in a memory and analyzed later.

Computing devices may further include systems such as a separate speech receiving device (for example, a wrist mounted device), processor module (for example a belt mounted computer comprising a processor, memory, and plug-in hardware module comprising a speech recognition system), and display device (for example, a visor-mounted display). Preferably components are in wireless communication and function as a unitary device.

Wireless transmission methods can include Bluetooth, a wireless protocol developed by Ericsson (Sweden) and others, IEEE802.11(b) and similar, local wireless networks such as wireless Ethernet, IR, optical, and ultrasound methods. Wireless transmission methods between devices offers improved convenience, however cable connections can be used in place of wireless methods.

U.S. provisional application Serial No. 60/212,319 to James R. Mault (filed Jun. 16, 2000) is incorporated herein by reference.

DETAILED DESCRIPTION OF THE INVENTION

Figure 1:
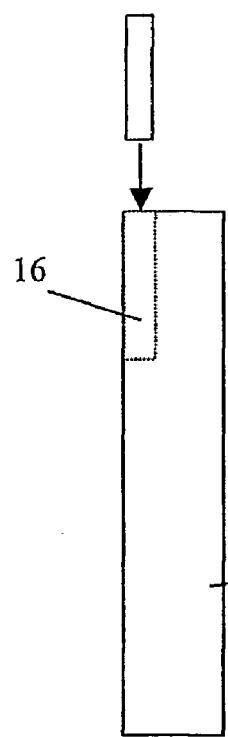
FIG. 1 shows a hardware module being inserted into a portable computing device.
Figure 2:
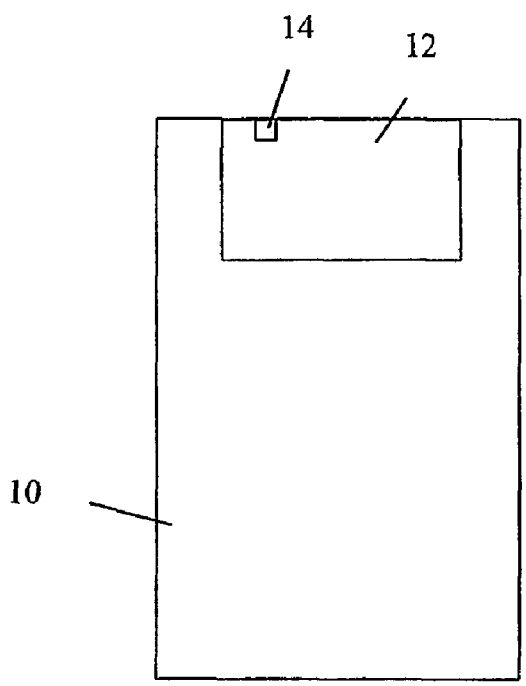
FIG. 2 shows a portable computing device having an inserted hardware module.

According to the present invention, a hardware module is provided which interconnects with a portable computing device, such as a PDA. The hardware module includes a microphone for receiving speech and may include other controls such as an on-off switch and sensitivity adjustments. An example of the present invention is shown schematically in FIGS. 1 and 2. The portable computing device 10 receives a hardware module 12 which, in the Figures, slides into a slot 16 in the back side of the portable computing device 10. The hardware module 12 includes a microphone 14 located near the edge of the module so that it is on the upper side of the portable computing device in use. In portable computing devices already including a microphone, the microphone may be omitted from the module. The module preferably includes both hardware and software so that when it is inserted in the slot in the portable computing device, the portable computing device becomes capable of simplified speech recognition.

Figure 3:
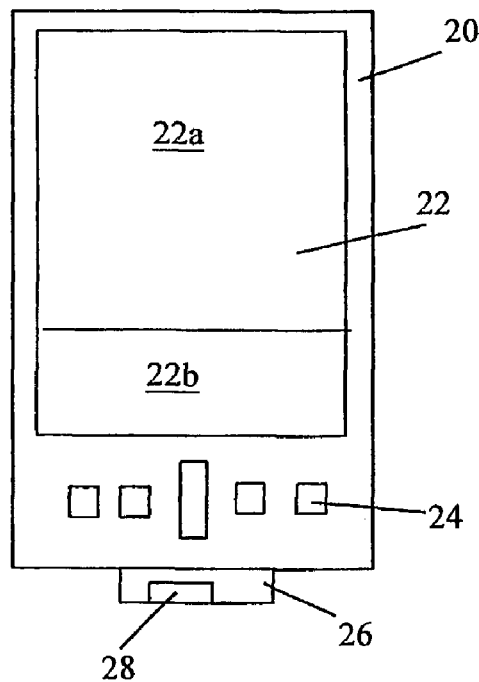
FIG. 3 shows a portable computing device having an inserted hardware module.

FIG. 3 shows another embodiment, in which module 26 is inserted into a slot in the lower edge of a portable computing device 20. Part of the module is exposed, allowing a person to speak into microphone 28. The portable computing device has display 22 and data entry keys 24. The display is divided into a menu display area 22a and a user instruction area 22b. However, this division is not critical to embodiments of the present invention.

Figure 4:
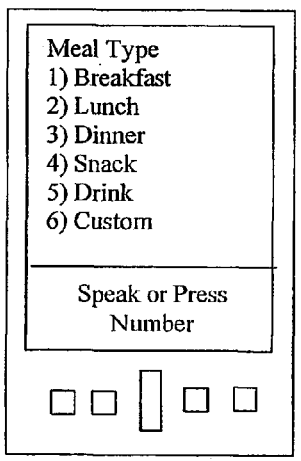
FIGS. 4-6 show possible menu presentations on the display of a device, by which a person can select a cereal name to add to a diet log.
Figure 5:
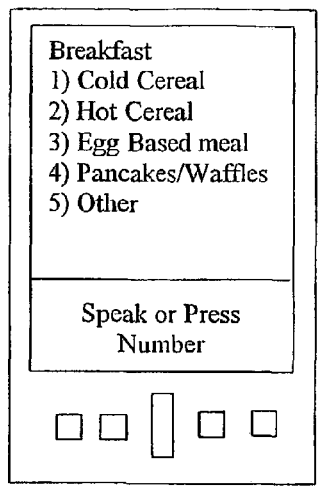
Figure 6:
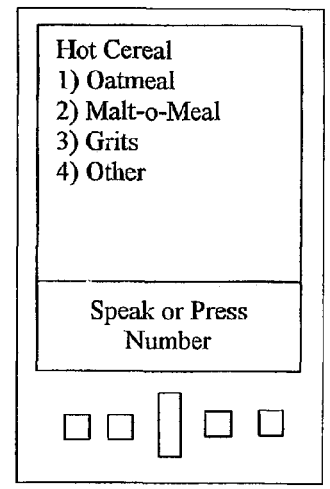

Referring now to FIGS. 4-6, an example use for the simplified speech recognition module will be explained. In the Figures, a portable computing device is shown displaying textual menus for providing a number of choices. The hardware module is not shown. In this example, the portable computing device is being used to record dietary intake. In FIG. 4, the portable computing device presents a menu with six options for meal type. Software providing the dietary intake software may be part of the hardware module, an additional module, or may be software loaded into, or already part of, the portable computing device. Using the speech recognition module, the person merely speaks the number of their choice of meal type. For example, if the person wishes to input information related to breakfast, they say the word "one." This is equivalent to entering the number 1 using the stylus or button on the portable computing device. This choice brings up a second menu, as shown in FIG. 5. In this menu, several breakfast choices are displayed. If the person wishes to choose hot cereal, they pronounce the word "two." This, once again, enters the choice into the software causing the software to bring up a third menu, as shown in FIG. 6. This third menu presents a variety of choices for hot cereal. It will be clear to those of skill in the art how this process may continue, in a very simplified manner, allowing a person to choose items for their diet. The chosen items, and associated nutritional data, can then be stored in a diet log for the person. This method may be similarly applied to data entry chores such as expense account tracking.

As known to those of skill in the art, a very wide variety of software applications are available for portable computing devices. According to the present invention, the hardware module and the software it carries are designed to work with many of the software applications. That is, the hardware and software module integrates with and communicates with a portable computing device such that speaking a number provides the same input to the software running on the portable computing device as if the person had used a stylus to input the number. Also, additional vocabulary may be provided in the same hardware module, or another hardware module according to the present invention. For example, many portable computing device functions require the use of up and down buttons. For this purpose, the hardware module may also recognize the commands "up" and "down.". Commands could also be recognized for a few of the most commonly used functions of the portable computing device, such as "date" for date book, "to do" for the to do list, and "address" or "phone" for the address list, and to change operating modes of the portable computing device. The hardware module may also recognize a few letters such as A through J, or the entire alphabet, a set of alphanumeric characters, or a set of words corresponding to characters, for example alpha, bravo etc. for the alphabet A-Z. In addition, a small number of extra words such as back, delete, enter, and the like, for simple navigation can be added to the limited list recognized. Obviously, the speech recognition capabilities are entirely dependent on the complexity of the hardware and software in the module. Therefore, for some applications a very simple speech recognition module may be sufficient. In this case, recognizing numerals 0 through 9 may be more than sufficient. As the software and hardware capabilities of portable computing devices improve, more complex modules may be desirable for some applications.

The hardware module can be a proprietary accessory to a portable computing device, or may comply with well known standards, for example PCMCIA and Miniature Card standards. The design of an accessory module with imaging capabilities, which may be advantageously modified for use in the present invention by inclusion of a voice recognition system, is disclosed in U.S. Pat. No. 6,219,560 to Erkkila et al., incorporated herein by reference.

As will be clear to those of skill in the art, the present invention provides numerous advantages in the input of data. In the example given earlier in entering diet information, the person may simply enter their choices by quickly repeating the words "one," "two," "one." This may be both easier and more pleasant than manual input for many persons. Also, some persons may have limited dexterity, making use of a stylus, keyboard, or other manual entry mechanism very difficult. The speech recognition module allows single handed, or even hands free, use since the stylus need not be grasped.

In other embodiments, a voice reception module comprising a microphone and a transmitter can be mounted near the person's mouth, such as on a collar, or the skin, and transmit audio signals to a computing device, such as a PDA, desktop computer system, remote server, interactive television set top box, and the like. The person can view a menu presented on the display of a computing device, and select items using speech commands directed to the microphone. The voice reception module can further comprise an oscillator, such that the signal received by the microphone is modified by the shape of the person's mouth, for example by the action of forming words (such as letters, numbers, food names) so that, for example, the person can provide commands to the computing device by silently forming words without the need to speak audibly.

Diet Log

As described above in relation to FIGS. 4-6, speech control of menu selections is useful in creating a diet log. In U.S. Pat. Nos. 5,704,350 and 4,891,756, incorporated herein by reference, Williams describes the selection of food items through a hierarchical menu system. This hierarchical approach can be advantageously combined with speech recognition for diet log creation. A diet log software application program was also described in U.S. Provisional Pat. App. No. 60/240,185, filed Oct. 13, 2000, incorporated herein by reference. This program can be advantageously modified for use with embodiments of the present invention by adapting the menu selection methods provided by the software program to be responsive to spoken commands, as interpreted by a speech recognition system. Other diet log software are known in the art, for example as described by Kretsch in U.S. Pat. No. 5,233,520.

Figure 7:
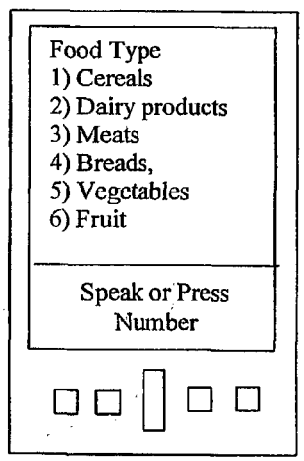
FIGS. 7-9 show other possible menu presentations on the display of a device, by which a person can select a cereal name to add to a diet log.

In embodiments of the present invention, the person is initially presented with a high-level menu of food types, such as a menu listing as shown in FIG. 7. As described above, the person can speak the number associated with each food type identifier. The person may also speak a letter corresponding to the first letter of one or more of the menu listings. The menu listing can be reduced to a unique item, which is then selected, or to a number of items each beginning with the spoken letter. The person can then speak a second letter to further restrict the selection, and a third letter if necessary.

If multiple word listings are presented to the person, a second (or later) spoken letter can be applied to restrict choices to those having a second word beginning with that letter. For example, if breads are listed in a menu as bread, rye; bread, brown; bread, pumpernickel (and the like), a person may speak "B . . . R" to select bread, rye.

With respect to FIG. 7, a person may speak "1", or "C" to choose cereals. In other embodiments, the vocabulary of the speech recognition system is automatically restricted to the words and numbers displayed on the menu. In this case, the word "cereals" can be reliably distinguished from the other word options by a speech recognition system. In this case, the first syllable alone can be used to distinguish the word "cereals" from the other choices.

Figure 8:
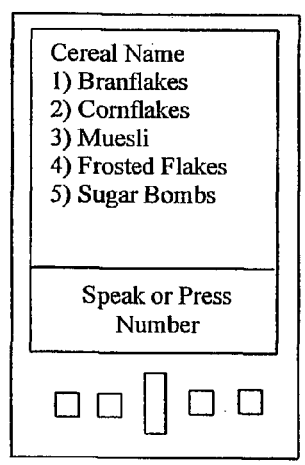

FIG. 8 shows another menu of food item identifiers which may be presented to the person after the person has chosen cereals from the menu of FIG. 7.

Figure 9:
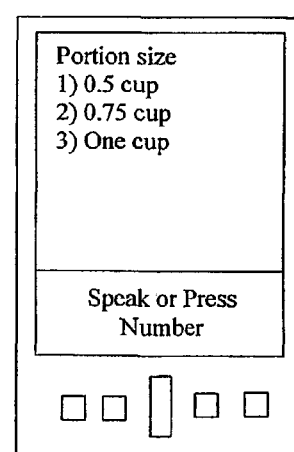

FIG. 9 shows a portion size menu which may be presented to the person after they have selected a food item identifier.

Figure 10A:
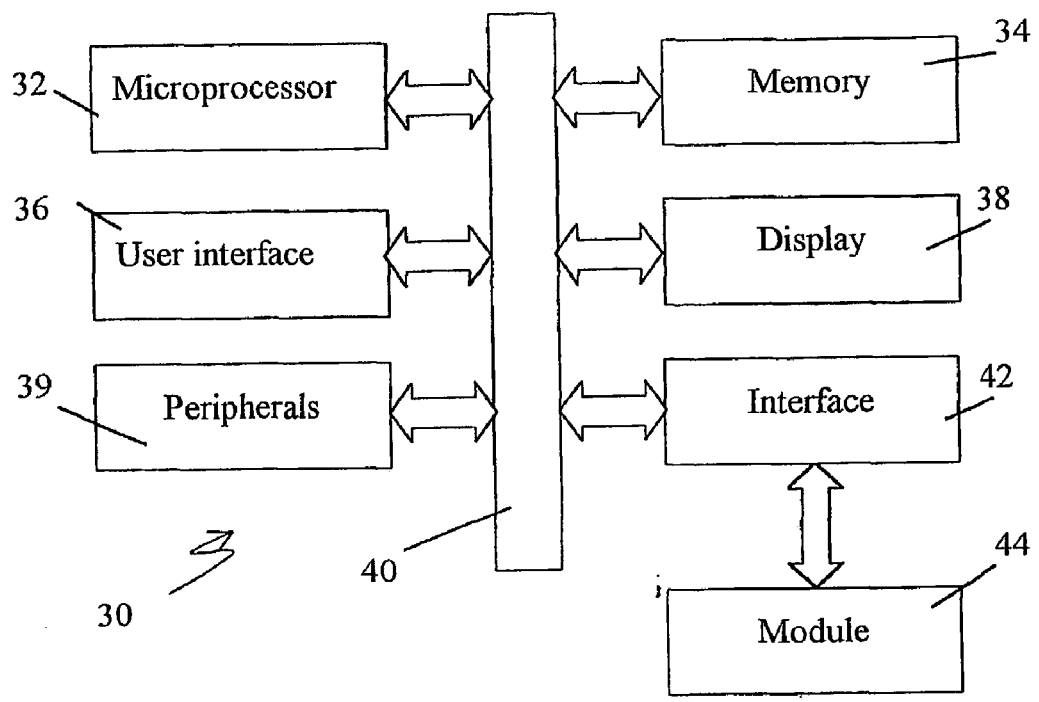
FIG. 10A shows a simplified schematic of a portable computing device which may be used in embodiments of the present invention.
Figure 10B:
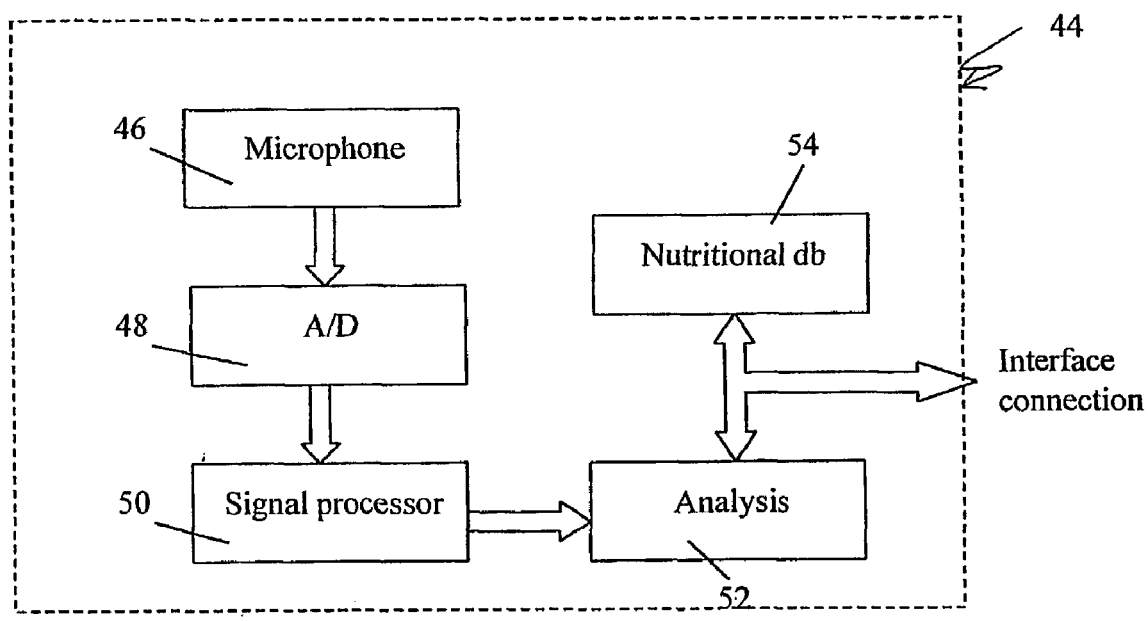
FIG. 10B shows a simplified schematic of a hardware module which may be used in embodiments of the present invention.

FIG. 10A shows a schematic of a portable computing device which may be used in embodiments of the present invention, comprising microprocessor (processor) 32, memory 34 (which may comprise ROM, RAM, memory modules, and other memory types and combinations), user interface 36 (which may comprise buttons, stylus, and other mechanical data entry mechanisms), a display 38 (comprising a display driver), peripherals 39 (which may comprise an additional display, indicator, printer, buzzer, speaker, modem, drive, and the like), accessory interface 42, and hardware module 44. FIG. 10B shows a possible schematic of a hardware module 44 for use in embodiments of the present invention comprising a microphone 46, analog to digital converter 48, signal processor 50, speech analysis circuit 52, and nutritional database 58. In this example, commands such as numeric speech are interpreted by the analysis circuit 52, which sends a corresponding electrical signal to the interface 42, for interpretation by the microprocessor 32. The nutritional database can also be accessed by a software application program running on the portable computing device. In other embodiments, the module 44 may further comprise a processor and additional memory, and diet log software may run on the module, displaying information on the display 38, and storing a diet log either on the memory of the module, in the memory 34, or at a remote location such as a remote computer accessed over a communications network.

Figure 11:
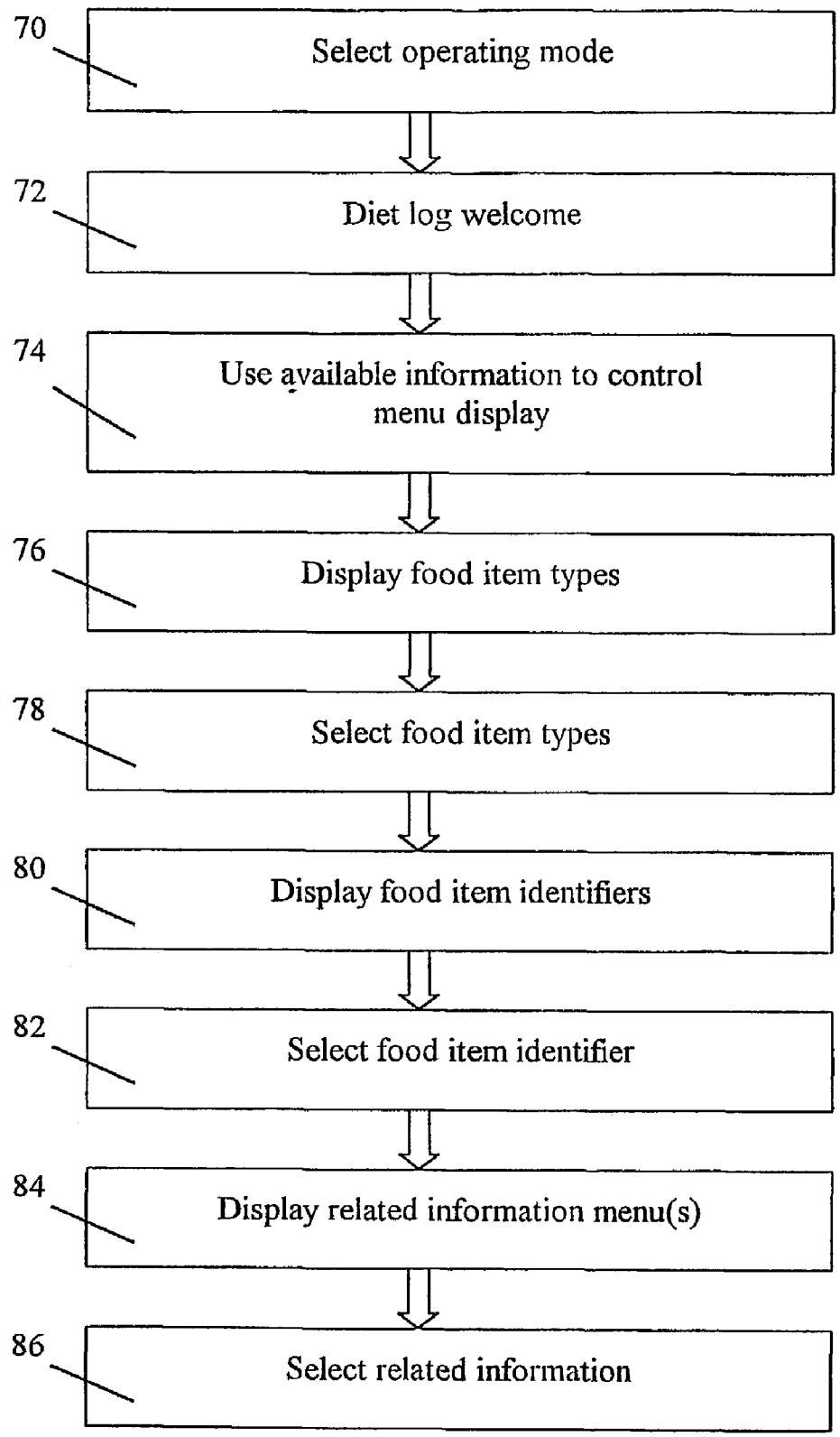
FIG. 11 is a flowchart illustrating a method of diet logging.

FIG. 11 shows a method of creating part of a diet log according to the present invention. Box 70 corresponds to the selection of the operating mode of the computing device, for example by speaking the word "diet". Other words which may be recognized at this stage might include exercise (for exercise logging), balance (for calorie balance calculation), address (for address book), and the like. Box 72 corresponds to the presentation of a diet log welcome screen to the person, possibly including a summary of data entry methods. Box 74 corresponds to the use of available information to modify presentation of menus to the person. Box 76 corresponds to the presentation of types of food to the person, for example as appropriate for the time of day, or other information determined in step 74. Box 78 corresponds to the selection of a type of foods, for example using voice recognition methods. Box 80 corresponds to the display of food items according to the selected food type. Box 82 corresponds to the selection of a food item by identifier, for example by a particular name or code. Box 84 corresponds to the display of a menu of related information. Box 86 corresponds to the selection of related information.

With regard to Box 74, available information can include location, purchase information, time, known preferences, known meals supplied by a weight control business, dietary goals, and the like. The information can be in the memory of the computing device, received over a communication network, preprogrammed, based on previous behavior, or determined using other methods and sources. For example, at times corresponding to lunch times, a lunch menu can be presented. Other meal and snack times can be correlated with the consumption of certain foods, possibly using previously collected data. If the location of the person is known (for example using global positioning, cell phone triangulation, or local wireless network based methods) the menu can be presented accordingly. A person in a particular restaurant can be presented with diet log options corresponding to that restaurant. A person at home can be presented with lists of food known to be at home, for example using prior purchase information or known preferences. If the person as at a business office, typical foods consumed there can be presented as a menu. There is often a strong correlation between a person's location and the foods that they consume. This correlation can be established by a software learning process, or can be preprogrammed, or entered by the person. The food-location correlations can then be used to restrict menu presentation to the person. If food has been obtained from a vending machine or similar food dispensing machine, or such a machine is detected nearby, menus corresponding to available foods can be presented. Personal expenditure information can also be used, for example if a transaction has taken place at a restaurant or food retail establishment, that information can be used to help determine food consumed. If the identity of a previously purchased meal is known, for example using a credit card transaction log, the identity of the food can be entered into the diet log and the methods of the present invention can then be used to record the amount of food eaten, for example as a fraction of serving size.

With further regard to Box 86, further information can comprise portion size, preparation method, accompanying items or omissions, fraction of meal eaten, and the like. For example, if the person chooses cornflakes as the food item identifier, the person can then be asked to enter portion size and amount of milk. This can be done by presenting a menu of options and receiving spoken choices, possibly using more than one menu depending on the food item selected in box 82.

Figure 12A:
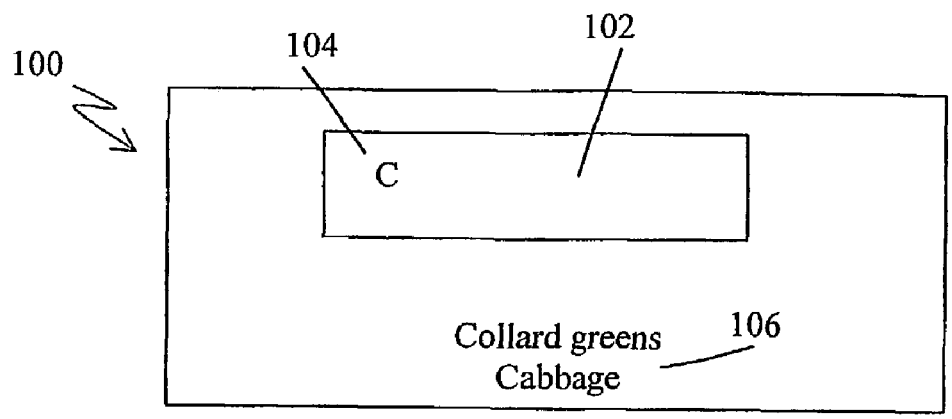
FIG. 12A shows a presentation on a display, whereby a recognized letter is used to restrict menu presentation.

FIG. 12A shows a display (100) of a computing device having a window 102 displaying received speech commands. In this example, the letters A-Z are used for speech commands, but other limited vocabularies such as numbers can also be used. The person has spoken the letter "C", which is recognized by the speech recognition system and displayed at location 104 in window 102. A menu of food item identifiers (or types, according to the diet log method and hierarchy in use) beginning with the letter "C" is displayed. If the person has just eaten cabbage, the person then speaks the letter "A" to distinguish it from the other displayed option. Further letters can be entered to further restrict the menu if necessary, with an item being selected once it is the only menu option remaining. The word "Back" (or similar) can be recognized to delete a displayed letter and remove the corresponding restricted selection of food item identifiers.

Figure 12B:
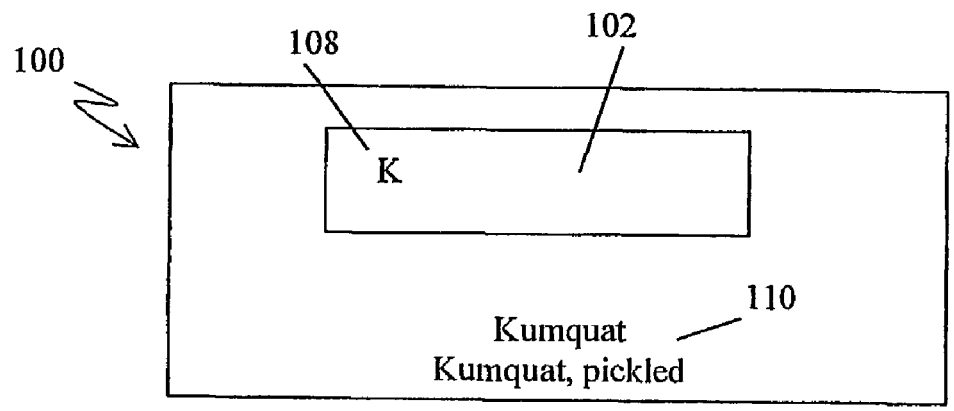
FIG. 12B shows a further presentation on a display, whereby a recognized letter is used to restrict menu presentation.

FIG. 12B shows the letter "K" displayed in window 102, and two diet log options presented, kumquats and pickled kumquats. In this case, the pickled option can be selected by speaking the letter "P", the first letter of the second word. This general approach is valuable in diet logging, as often a single food item name will be repeated with several modifiers, or plural modifiers. In this case, speaking the first letter of the base name (e.g. "M" for milk), and the first letter of the modifying term(s) (e.g. "S" for skim), can be used for rapid speech-recognition selection of diet log items. The first letter of the base name can be repeated to select the base (unmodified) items. Other letters or numbers can be entered to differentiate ambiguities if necessary. Alternatively, the modifiers can be numbered and the person speaks a number corresponding to the modifier. In more advanced systems, the recognized vocabulary of the speech recognition system is restricted to the options presented to the person, which considerably increases the reliability of the speech recognition system over one trying to match spoken commands to a large available vocabulary. In some embodiments, only the first spoken syllable, or first two syllables, are used for speech recognition.

Nutritional Database

The hardware module described above can comprise a memory containing a nutritional database. This database comprises food item identifiers, such as the names of foods, meals, beverages, diet supplements, and the like. The data can be arranged in a hierarchical fashion, so that food item identifiers are grouped by generic type, such as: meat products, dairy products, starches, preferred meals, lunch items, breakfast items, dinner items, meal supplements, nutraceuticals, prepackaged foods, and the like. The generic types can further be grouped into higher level groups, or divided into subgroups, if convenient. Presented menus can in certain cases comprise both food types and specific food identifiers.

A nutrition database can also be contained in the memory of a portable computing device, or on a memory module which may be inserted into the portable computing device or the hardware module described above, using a memory module slot.

The nutritional database can also be located on another computer system, memory module, or device in communication with the portable computing device, as will be described in more detail below.

Food items can be added to the nutritional database using the available data entry mechanisms of the portable computing device, or using data received over a communications network or memory module transfer.

Communications Network

The portable computing device can be in communication with a remote computer system over a communications network such as the Internet. For example, the portable computing device can be in wireless communication with the Internet through an Internet service provider (ISP), and then through the Internet to a remote server system. (The ISP is considered part of the communications network). In this case, the nutritional database and speech recognition system can be located on the remote computer system.

In other embodiments, a voice signal, for example as provided by a microphone or other speech receiving device, can be transmitted over the communications network to a remote computer system, which can comprise a speech recognition system. A diet log software application can be executed by the portable computing device or remote computer system. Menu displays, nutritional information, diet advice, and the like can be presented on the display of the portable computing device. The necessary bandwidth for uploading voice signals will likely be much less than that necessary for downloading visual data from the remote computer system to the portable computing device. Hence, different communications networks can be used for data transfer to and from the portable computing device. For example, a wireless phone system can be used to transmit voice data to the remote computer, and a higher bandwidth wireless connection to an Internet service provider can be used to receive data for presentation on the display.

Figure 13:
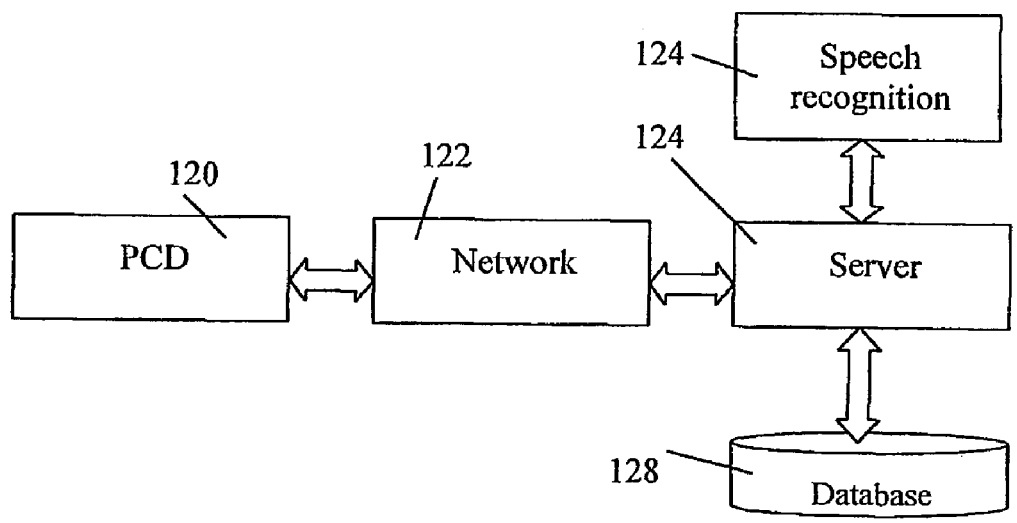
FIG. 13 shown a schematic of a system in which the nutritional database and speech recognition system are accessed using a communications link to a remote server.

FIG. 13 shows a portable computing device 120 in communication with a remote server system 124 over communications network 122, which can be the Internet. Spoken commands received by the device 120 are transmitted as digitized audio files to the server 124, which directs them to the speech recognition system 126. The spoken commands are then converted into computer-readable commands (electronic commands, or speech command signals), and a server software application program can responds to the electronic commands by selecting data from the nutritional database. Menus generated by the server software application program can be viewed on the display of the computing device 120.

Product Codes

As part of a weight control program, a weight control business can supply a person with prepackaged meals. These can be identified using abbreviated codes for convenient entry into a diet log. For example, a lunch can be identified by a code such as L1, which can be readily entered into a diet log by speech command or other method. The nutritional database can further be supplied by the weight control business, so as to contain nutritional information correlated with each product code.

Product identities and/or nutritional content can be algorithmically converted to a numeric (or alphanumeric) code, analogous to Gemstar VCR Plus codes. This facilitates the entering of this simplified data into a diet log by speaking the code characters.

Exercise Log

The person can also record exercises on the portable computing device in an analogous manner. Exercises and activities can be grouped in a hierarchical fashion within an exercise database, contained within the memory of the portable computing device, a module, or other device in communication with the portable computing device. The portable computing device can have several operating modes, such as diet log, exercise log, calorie balance calculator, time display, position display, organizer, word processor, and the like, and can be switched between modes by any convenient method.

Calorie Balance

The person can determine their resting metabolic rate (RMR) using a metabolic rate meter such as an indirect calorimeter. The RMR can be entered into the portable computing device by any convenient method, such as be speaking the digits combined with speech recognition. The calorie management software can then be used to calculate calorie balance using diet log entries, exercise log entries (and/or estimated activity levels), and RMR.

PDA-Cell Phone

As is known in the art, a portable computing device such as a PDA can be readily combined with the functionality of a wireless telephone into a unitary device, which we will term a DAP (digital assistant—phone). In this case, a microphone will be present in the DAP and can be used for speech command operation of a diet log software. The speaker of the DAP can be used to provide feedback to the person, such as noises to indicate successful or unsuccessful speech recognitions. The term portable computing device, as used herein, includes devices with additional functionality such as a DAP.

Using a portable computing device with a speaker, speech synthesis can be used to provide a dialog with the person, so that a display may not be needed for menu presentation. In this case, menus can be presented using synthesized speech. For example, a person speaks the word "Diet" to the portable computing device. The device responds "Diet Log Activated. It is now 12:10 pm. Lunch food types include 1—burrito, 2—sandwich, 3—yogurt, 4—other. Please speak number". The person speaks the number "1". The device responds "Burrito chosen. Choose 1—bean, 2—beef, 3—chicken.". The person speaks the number "3". The device responds "Did you eat the whole chicken burrito". The person responds "Yes". The device responds "OK. Chicken burrito entered into diet log. Don't forget your run this afternoon."

Interactive Television

A portable device can also be used for remote control of a digital interactive television or other entertainment device. Spoken commands can be transmitted to the set-top box of the digital interactive television, for example by speaking to the portable device with wireless transmission of a digitized audio file to the set-top box. The set-top box, or other device such as a remote server in communication with it, has a voice recognition system to convert the digitized audio file to electronic data, such as text and/or numbers. The electronic data can be used for channel selection of the digital interactive television, or selection from menus such as food item menus displayed on the digital interactive television. Spoken commands can be transmitted from a portable device, possibly with the form factor of a remote control, over a wireless telephone network to a remote computer having a speech recognition system, which then responds to the received and interpreted commands by providing corresponding visual menu presentations, selection indications, channel selections, program selections, and the like on the display of the interactive television.

Physical Location Determination

The portable computing device, or add-on hardware module, can further comprise a physical location determining unit, such as a global positioning system, triangulation system, or the like. The location can be correlated with positions of food retail establishments using a food retail database, and so with menus and available food lists. Hence, a portable computing device according to the present invention can present a food menu to a person based on the person's location. If the person is in a restaurant, a menu can be presented on a display of the portable computing device. The person can then select from the presented menu using the speech recognition systems described herein. A nutritional database is then used to assist in creating a diet log from the selected items.

Wrist-Mounted Device

Embodiments of the present invention can comprise a portable device supported by a strap around a wrist of the person, in the form of a wristwatch. The display of the device can be used to display time, other data, entertainment, and food menus to the person. A microphone in the housing can be used to receive spoken commands. A speech signal, such as a digitized audio file, can be transmitted to other devices carried by the person, or with which the person interacts (for example a PDA, desktop computer, entertainment device, remote computer, and the like). The display of menu options can be presented on the display of another device, such as a PDA.

Limited Display Capabilities

In some cases, display complexity will be insufficient to display all options to the person in the form of a menu. In this case, the person can speak the first letter of the required option, so as to limit the display to those food items or food types beginning with that letter. Other letters or numbers can then be spoken so as to further limit the display, or to select an item.

Other variations on the disclosed embodiments of the present invention will be apparent to those of skill in the art. These variations do not depart from either the spirit or scope of the present invention, and therefore the disclosed embodiment should be interpreted broadly.

Having described my invention, I claim:

1. A diet logging module for a portable computing device comprising:

a module housing configured to engage with an accessory interface of the portable computing device;

a memory storing a database of nutritional data relating to each of a plurality of food item identifiers, each food item identifier comprising an alphanumeric character;

a display, adapted to display at least one menu of a set of hierarchical menus of objects related to consumption of a food item of the plurality of food items, each object of the menu of objects identified by a corresponding object identifier, each object identifier comprising an alphanumeric character;

a speech receiving device, adapted to receive a speech command from a user, the speech command comprising an alphanumeric command corresponding to an object identifier or a food item identifier;

a speech recognition system, adapted to receive the speech command from the speech receiving device, and to display a subsequent menu of the set of hierarchical menus in response to the speech command;

a location determination component, adapted to determine a location of the portable device in operation by the user; and a display process to display one or more food items determined by a food item identifier received by the speech recognition system, and further determined by the location of the portable device as determined by the location determination component.

2. The diet logging module of claim 1, wherein the location determination component is selected from the group consisting of a global positioning system, a cell phone triangulation system, and a wireless network based location system, and further comprising a correlation module that uses a food retail database to provide one or more lists of food items from one or more food retail establishments to the display process based on the location of the user.

3. The diet logging module of claim 2, wherein the display process displays a list of menu items to the user from the one or more lists of food items based on the location of the portable device, and further comprising a time determination means, and wherein the display process displays at least certain food items from the one or more lists of food items based on the time of operation by the user.

4. The diet logging module of claim 3, wherein the software application program is adapted to select a selected food item identifier from the nutritional database in response to a speech command received for a food selection menu of the hierarchical set of menus, the food selection menu including a plurality of different food items corresponding to parameters specified in previously displayed menus of the hierarchical set of menus.

5. The diet logging module of claim 4, wherein the software application program is further adapted to store the selected food item identifier and associated nutritional data in the memory so as to create a diet log generated by the diet log process.

6. A portable computing system comprising:
   a display;
   a microprocessor;
   a memory;
   a database of nutritional data relating to each of a plurality of food item identifiers, each food item identifier comprising an alphanumeric character corresponding to a unique food item;
   a speech recognition system providing an electrical speech command signal correlated with a spoken input;
   a location determination component, adapted to determine a location of the portable device in operation by a user; and
   a software application program, executed by the microprocessor, adapted to display a set of hierarchical selection menus, each menu of the set of hierarchical selection menus comprising an alphanumeric object identifier corresponding to a selection object, each selection object causing display of a subsequent menu of the set of hierarchical menus until a food menu is displayed, the food menu comprising selections obtained from a food retail establishment based on the location of the portable device, and wherein the food menu displays food item identifiers allowing a user to select a food item by uttering a speech command consisting of the alphanumeric food identifier corresponding to a selected food item, the software application program further configured to store nutritional data relating to the selected food item identifier in the memory so as to create a diet log of selected food items.

7. The portable computing device of claim 6, wherein the location determination component is selected from the group consisting of a global positioning system, a cell phone triangulation system, and a wireless network based location system.

8. The portable computing device of claim 6, wherein the set of hierarchical selection menus is selected from the group consisting of: meal type, food type, and portion size.

9. An accessory module for a portable computing device, the portable computing device comprising a microprocessor, a display, and an accessory port, the accessory module comprising:
   an electrical interface, adapted to communicate with the accessory port;
   a memory;
   a location determination component, adapted to determine a location of the portable device in operation by a user;
   a nutritional database, stored in the memory, correlating each of a plurality of food item identifiers with an associated food item nutritional content, each food item identifier of the plurality of food item identifiers comprising an alphanumeric character corresponding to a unique food item; and
   a software application program, stored in the memory, and executable by the microprocessor and adapted to display a set of hierarchical selection menus, each menu of the set of hierarchical selection menus comprising an alphanumeric object identifier corresponding to a selection object, each selection object causing display of a subsequent menu of the set of hierarchical menus until a food menu is displayed, the food menu comprising selections based on the location of the portable device; and wherein the food menu displays food item identifiers allowing a user to select a food item by uttering a speech command consisting of the alphanumeric food identifier corresponding to a selected food item, the software application program further configured, and further adapted to store the food item selection and correlated nutritional content within a diet log for the person.

10. The accessory module of claim 9, wherein the location determination component is selected from the group consisting of a global positioning system, a cell phone triangulation system, and a wireless network based location system.

11. The accessory module of claim 10, wherein software application program displays a list of menu items to the user based on the location of the portable device, and further comprising a time determination means, and wherein the display process to displays the one or more further corresponding to the time of operation by the user.

12. The accessory module of claim 9, wherein the speech command signal is provided by one of a speech recognition system resident on the accessory module, and a speech recognition system resident on the portable computing device.

13. A method of creating a diet log for a person, comprising:
   presenting a series of hierarchical food selection menus to the person, each food selection menu comprising an alphanumeric identifier corresponding to a selection related to a food item selectable by the person;
   receiving a type selection speech command from the person, the speech command comprising a spoken alphanumeric character for a menu item selected by the user;
   determining a location of the person;
   determining a time of presenting the series of hierarchical food selection menus to the person;
   displaying a subsequent food selection menu in response to the speech command, the subsequent food selection menu providing additional data relating to the selectable food item, wherein the selectable food item depends of the location of the person, and the determined time;

presenting a menu of food item identifiers to the person in a final food selection menu of the series of hierarchical food selection menus;

receiving a food selection speech command from the person, the food selection speech command comprising a spoken alphanumeric character for a selected food item; and storing the selected food item identifier and associated nutritional data within a memory device, so as to create a diet log for the person.

14. The method of claim 13, further comprising obtaining one or more lists of food items from one or more food retail establishments based on the location of the person, and wherein the selectable food item is selected from the one or more lists of food items.

15. The method of claim 13, wherein the menus are presented to the person on the display of a portable computing device carried by the person.

16. The method of claim 15, wherein the portable computing device comprises a wrist-mounted device worn by the person.

17. The method of claim 15, wherein the correlation of speech commands with selected identifiers is performed by a software application program running on the portable computing device.

18. The method of claim 15, wherein the correlation of speech commands with selected identifiers is performed by a software application program running on a remote computer system in communication with the portable computing device.

* * * * *